United States Patent [19]

Anton et al.

[11] Patent Number: 4,989,974
[45] Date of Patent: Feb. 5, 1991

[54] MICRO-FLOW CELL

[75] Inventors: Klaus Anton, Basel; Peter Dätwyler, Oberwil; Ernst Gassmann, Hofstetten; Peter E. Jordi, Basel; Nico Pericles, Herznach, all of Switzerland

[73] Assignee: Ciba-Geigy Corporation, Ardsley, N.Y.

[21] Appl. No.: 294,028

[22] Filed: Jan. 6, 1989

[30] Foreign Application Priority Data

Jan. 14, 1988 [CH] Switzerland .............................. 121/88

[51] Int. Cl.$^5$ ............................................. G01N 21/05
[52] U.S. Cl. ..................................... 356/246; 250/576
[58] Field of Search ................. 356/246; 250/343, 373, 250/576

[56] References Cited

U.S. PATENT DOCUMENTS

| | | | |
|---|---|---|---|
| 3,431,424 | 3/1969 | Allen | 356/246 X |
| 3,740,156 | 6/1973 | Heigl et al. | 356/204 |
| 3,810,695 | 5/1974 | Shea | 356/73 |
| 4,175,233 | 11/1979 | DePalma et al. | 250/343 |
| 4,477,186 | 10/1984 | Carlson | 356/246 |
| 4,643,570 | 2/1987 | Maechler et al. | 356/246 |
| 4,872,753 | 10/1988 | Danigel et al. | 356/246 |

FOREIGN PATENT DOCUMENTS 796745 6/1958 United Kingdom .

OTHER PUBLICATIONS

Analytical Chemistry 55, No. 14, 2459-60 (12/83).
Journal of Optical Society of America 40, No. 11, 757-760 (11/50).
Chromatographica 25, No. 1, 31-36 (1/88).

Primary Examiner—Davis L. Willis
Assistant Examiner—Matthew W. Koren
Attorney, Agent, or Firm—Harry Falber

[57] ABSTRACT

A micro-flow cell for chromatographic, spectrometric or scintillation measurements comprises a capillary tube, preferably made of glass or silica glass, through which flows the medium to be examined, and a holding device for said capillary tube. The holding device is separably composed of at least two parts which can be separated in their longitudinal direction. The capillary tube is fixed in the holding device by suitably formed connectors so as to be stress-free and tension-free to the greatest possible extent.

25 Claims, 2 Drawing Sheets

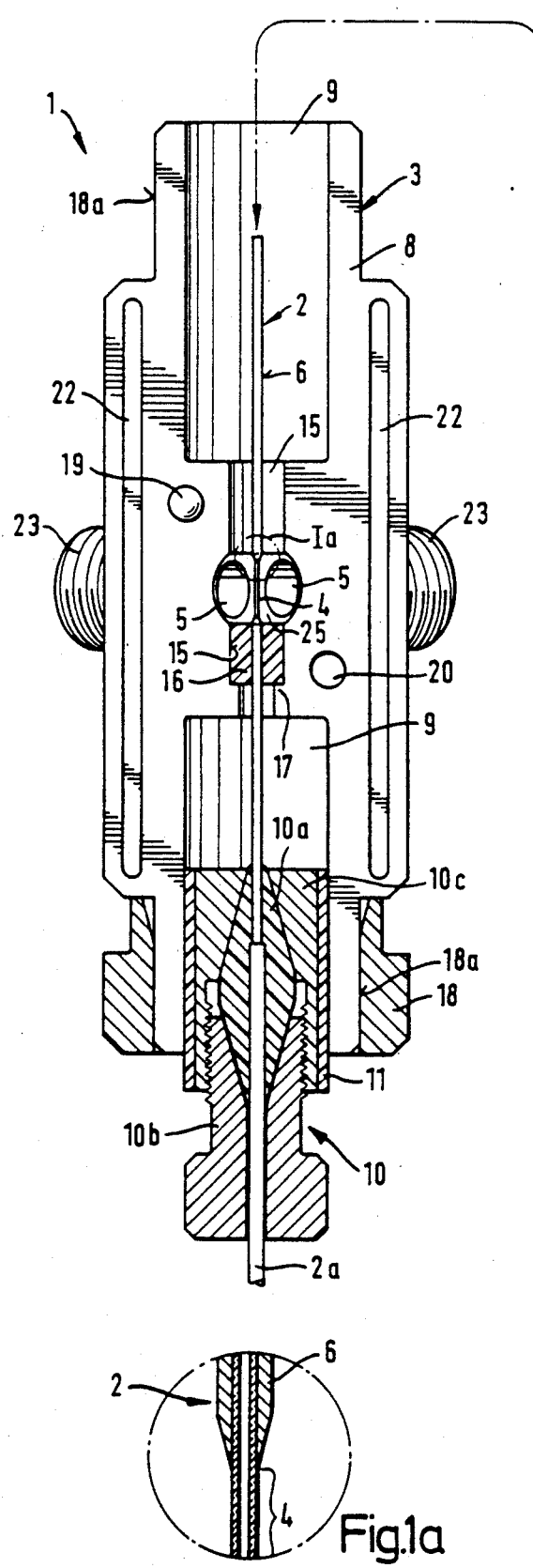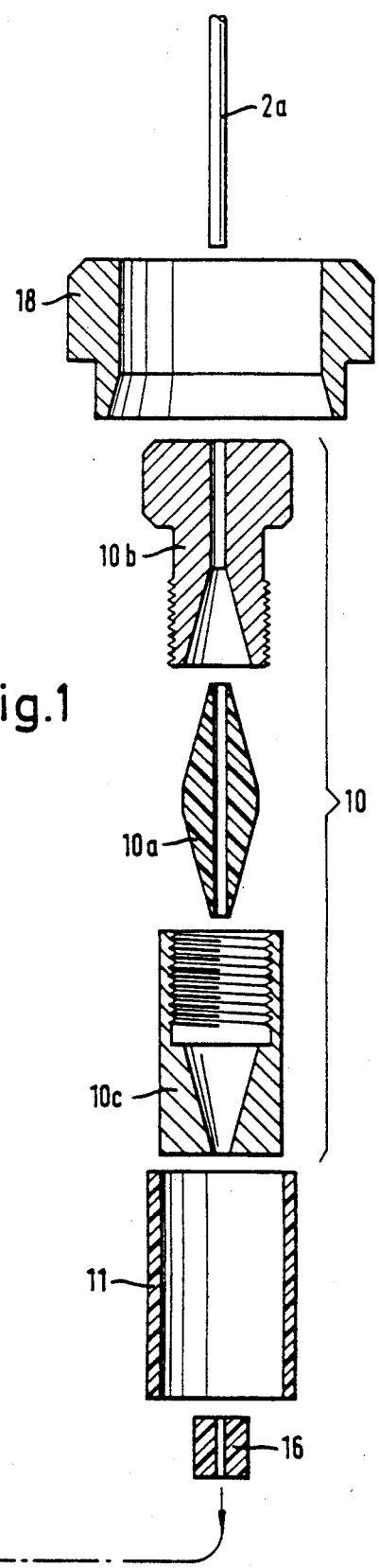
Fig.1
Fig.1a

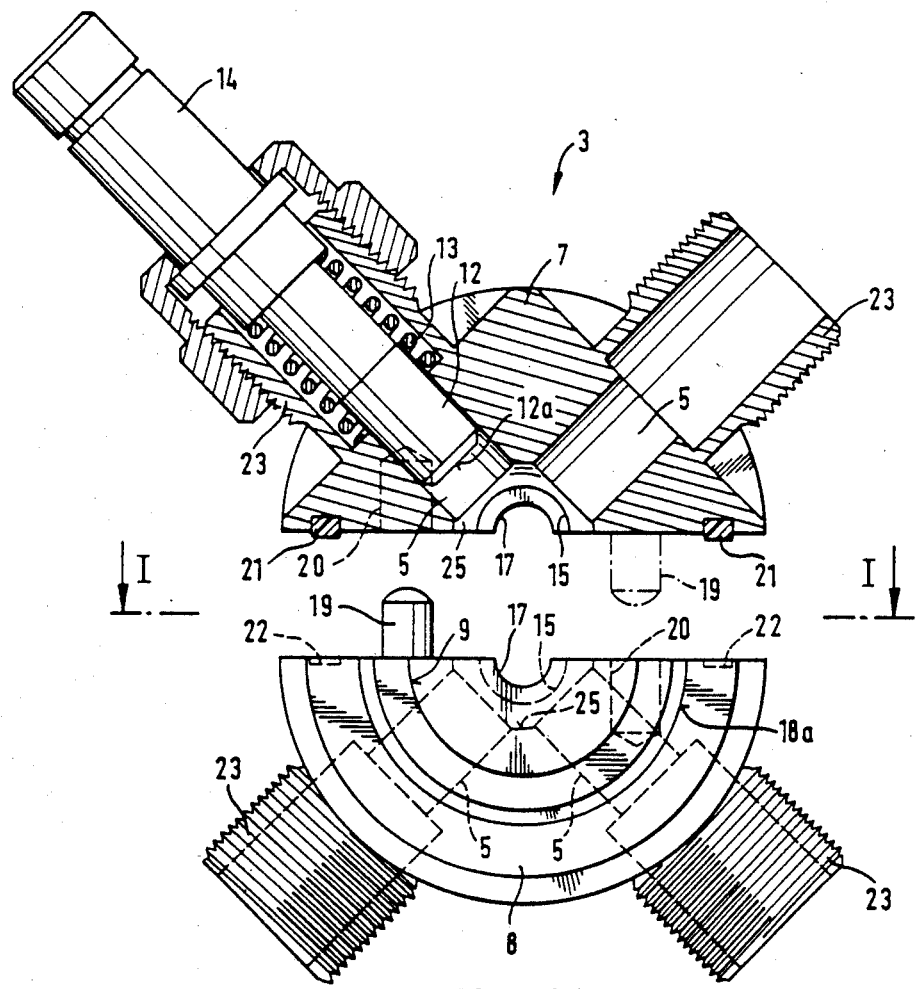
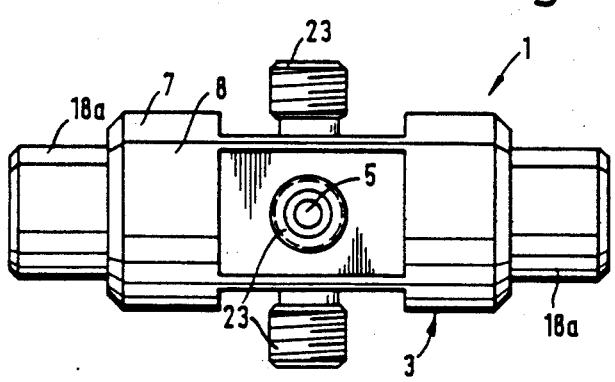
Fig. 2
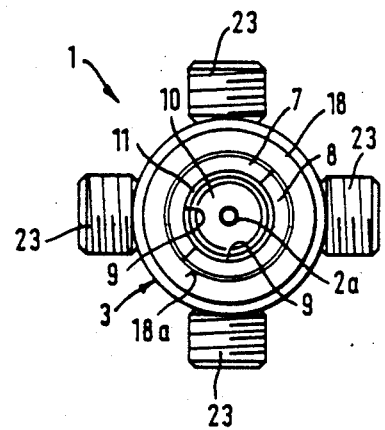
Fig. 4  Fig. 3

MICRO-FLOW CELL

FIELD OF THE INVENTION

This invention relates to a micro-flow cell for chromatographic, spectrometric or scintillation measurements.

In the field of liquid chromatography (LC), so-called supercritical fluid chromatography (SFC), gas chromatography (GC) and capillary zone electrophoresis (CZE), micro-column and capillary separation techniques are used for measurement and analysis Usually flow cells are used in these techniques in order to be able to carry out the measurements on a precisely defined volume in a precisely known environment. Optical absorption, reflectance, luminescence, emission and spectral-photometric processes are commonly used as measuring processes, but deposition rates in electrical fields are also investigated.

BACKGROUND OF THE INVENTION

A process of the latter type is described, for instance, in U.S. Pat. No. 4,175,233. In that process the deposition rate of solid constituents of the liquid to be examined (blood) are measured on germanium-coated glass plates. The glass plates, which are provided with electrode connections, are fitted into recesses in two shell halves and, together with two glass rods which are arranged on the longitudinal side between the glass plates, delimit, when the two shell halves are placed together, a cuboid space with open faces as the inflow and outflow of the flow cell. On the inflow and outflow sides there are provided two connections which are seated with flange-like widened parts in corresponding recesses in the shell halves. The connections each have at their opposite ends an annular groove which serves to fix a tube connection by means of a clamping ring. In a particular embodiment, one of the two shell halves has a light-permeable window in order to permit infra-red measurements as well. The two shell halves are held together in place by two clips. The flow cells thus formed are relatively large and accordingly insensitive to operate. Their range of use is mainly restricted to low-accuracy blood examinations.

Usually, however, flow cells are used which are designed first and foremost to carry out optical measuring processes. Such a flow cell is described in U.S. Pat. No. 4,243,883. This has a housing with a cover and, arranged inside the housing, a light source and a detector opposite it. The housing is provided with recesses to receive a coated flow tubing. In the measuring area between the light source and the detector, the cross-section of the tubing is narrowed and square in shape and equipped with windows in the coating which lie opposite each other. Said flow cell is used first and foremost for monitoring the blood of patients during operations, and the flow tubing must therefore have a fairly large cross-section. As a result of the integrated arrangement of the light source and the detector within the housing, the latter has relatively large dimensions and therefore can be operated relatively well. The possibilities for use of this flow cell are mainly restricted to the area stated.

Other, somewhat smaller flow cells are known from U.S. Pat. No. 3,728,032 and EP-A-No. 0,158,948. The two-part flow cell described in the US patent has an ellipsoid flow area with inlet and outlet openings lying opposite each other in the longitudinal direction of the cell. In the region of the measuring chamber where the diameter is greatest there are arranged two measuring windows lying opposite one another. The two halves of the flow cell, which are formed as mirror images, are connected by means of screws. The flow cell described in the European patent has convex depressions in the measuring area which are arranged in two halves which can be displaced longitudinally relative to each other in such a way that a winding flow area results. The flow cell has, in the measuring area proper, two measuring windows which lie opposite one another. The windows not formed with parallel planes but are spherically convex, so that they thereby function as lenses, which may have a nonnegligible influence on measurement.

In many chromatographic uses, the flow cells are made smaller still, and one speaks of micro-flow cells in this case. As a rule, a capillary tube, arranged in a housing and preferably made of glass or silica glass, as described, for instance, in "Analytical Chemistry", Vol. 56, No. 4, April 1984, pages 619A–629A, is mounted in the path of rays of a spectrometer and serves as a flow and measuring chamber. However, due to the very small dimensions of the capillary tube, problems then result with the reproducible placing thereof. Moreover, inexact gaps between the capillary tube and the detector of the spectrometer may also result. Both lead to increased noise and to drift phenomena during measurement.

A high-pressure-compatible capillary cell is required for the above-mentioned SFC-applications. It is even more unfavorable if the capillary tube is stretched within its holding device upon its placement or on connection to connecting capillary tubes;

It is an object of the invention to provide a micro-flow cell in which the fixing of a capillary tube within its holding device is simplified and is designed in such a way that a fast, reproducible connection is made possible between the holding device and the capillary tube without deformation arising, either during assembly, or due to changes in stresses during operation or by heat transfer.

It is a further object to provide a micro-flow cell which is high-pressure-compatible.

According to the present invention there is provided a micro-flow cell for chromatographic, spectrometric or scintillation measurements, comprising a capillary tube with an inlet and outlet and defining a flow path between said inlet and outlet for a medium to be examined, a first holding part for said capillary tube, a second holding part for said capillary tube, the two holding parts being adapted to be secured about the length of the capillary tube to hold the latter, and being separable along their longitudinal direction, at least one window for the transmission of measuring light to said tube formed in at least one of said holding parts, means for connecting each end of the capillary tube in a flow path for said medium, and means for locking said holding parts together about said capillary tube.

BRIEF DESCRIPTION OF THE SEVERAL VIEWS OF THE DRAWINGS

In order to enable the invention to be more readily understood, reference will now be made to the accompanying drawings, which illustrate diagrammatically and by way of example an embodiment thereof, and in which:

FIG. 1 is a longitudinal section through a micro-flow cell in a view which is exploded on one side, the sectional plane running exactly along the contact surfaces of two halves or shell halves forming a holding device, FIG. 1a shows a detail (Ia) of FIG. 1 on a larger scale, FIG. 2 is a view showing one half or shell half in a partly sectional view and a front view of the second half of the holding device, FIG. 3 is a front view of the assembled micro-flow cell, and FIG. 4 is a side view of an assembled micro-flow cell holding device without connectors and clamping rings.

DETAILED DESCRIPTION OF THE INVENTION

Referring now to FIG. 1 of the drawings there is shown a micro-flow cell 1 for chromatographic or spectrometric measurements. The cell comprises a capillary tube 2, preferably made of glass or quartz, through which the medium to be examined is intended to flow, and a holding device 3 for said capillary tube 2. Light-permeable areas 4 or passages 5 for the measuring light are provided on the capillary tube 2—if this is provided with a coating or a covering—and on the holding device 3, two passages 5 in each case lying diametrically opposite one another. The term "measuring light" is understood to be ultraviolet, visible and infra-red light.

If the capillary tube 2 is coated with a coating 6 for the purpose e.g. of stabilising the tube, the light-permeable areas 4 on the capillary tube 2 are formed due to the fact that the coating is removed or omitted, as is described, for instance, in the document cited earlier, "Analytical Chemistry".

It can be seen from FIG. 2 that the holding device 3 comprises two substantially identical shell halves 7 and 8 which have plane-parallel contact surfaces.

The shell half 8 shown in FIG. 1 and its counterpart, the shell half 7, each have on both front faces recesses 9 which are open at the front face and which continue into the shell halves 7 and 8. These are designed to receive connectors 10 for the capillary tube 2. Each connector 10 comprises a clamping insert formed with a central bore or an elastic ring part 10a which can be inserted into an appropriately formed bore of a cylinder part 10c provided with an internal thread. Said two connector parts (elastic ring part 10a and cylinder part 10c) may be pushed onto the capillary tube 2. By axially screwing a screw part 10b provided with an external thread and a central bore into the cylinder part 10c, the elastic ring part 10a is deformed axially and hence also radially and thus the capillary tube is gripped.

It is sufficient to place the capillary tube 2, which is provided on both sides with the connectors 10, into a shell half 8 and then to add and close the second shell half 7 from the other side in order to produce the micro-flow cell 1, the capillary tube 2 being fixed in the holding device 3 without stress. Connecting capillary tubes 2a may then be connected to the connectors 10 in the conventional manner, unless a continuous capillary tube 2 is used.

Larger differences in diameter between the cell capillary tube 2 which is clamped in the holding device 3 and the connecting capillary tubes 2a may also be compensated by suitable configuration of the bore of the elastic ring parts 10a.

An important and advantageous embodiment of the micro-flow cell I, which also permits tolerances during production and assembly and e.g. stress movements produced by pressure and heat to be taken up, is one in which the connectors 10, which can be inserted into the recesses 9 of the holding device 3 with an accurate fit, have on their outside an elastic coating e.g. in the form of a heat-shrinkable sleeve 11, which can be gripped upon insertion of the connectors 10 into the recesses 9 or conversely, upon attaching the recesses 9 to said connectors 10 and upon closing the holding device 3 so that the connectors 10 are slightly elastically displaceable radially and axially. In this embodiment, a very slight ability to be displaced is sufficient, as the capillary tube 2 itself is of only very small dimensions. In this manner, any stress movements or tolerances can be compensated so that the capillary tube 2 is largely kept free of stresses. At the same time, a sufficiently great clamping force can also be transmitted via such an elastic coating or a heat-shrinkable sleeve 11 so that the capillary tube 2 remains fixed and gripped even at a high internal pressures of up to 500 bar and more. Furthermore, the heat-shrinkable sleeves 11 represent seals with respect to the recesses 9 on the front face of the holding device 3 and prevent the undesirable ingress of unwanted light.

The holding device 3 shown in FIGS. 2 and 3, has four radial, continuous passages 5 which extend as far as the capillary tube 2 located in the interior and which are arranged in a plane of cross-section. At least one pair of passages 5 which are located opposite each other serve as measuring orifices for the measuring light, while the other pair of passages are provided for additional measurements and/or for observation. Thus, for example, the attaching and advance in one pair of passages of photoconductors 12 until directly in front of the capillary tube 2 may be observed by attaching a microscope to one of the other pair of passages. If necessary, however, three such passages 5 or in special cases only two such passages 5, which may be at an angle to each other, also suffice, as, for instance, in the case of fluorescence measurements, the measuring light being beamed axially into the capillary tube 2 and the fluorescence beam being detected at one or both measuring orifices.

In a particular form of the holding device 3, only one shell half 7 or 8 has a radial passage 5. In this case the second shell half 8 or 7 is provided on its inner wall with a reflective surface which is arranged exactly opposite the opening of the passage 5. The measuring light is beamed in through the single passage 5, reflected on the reflective surface and passed out again through the passage 5 and passed to the detector.

In FIG. 2, a photoconductor 12 and its photoconductor connector 14, which can be connected against the force of a spring 13, are shown inserted into one of the measuring passages 5. The passage which directly adjoins it and is arranged at right-angles thereto permits observation of the attaching process so that it can be ensured that the photoconductor 12 and in particular its front face 12a are arranged in the correct position relative to the capillary tube 2 and its light-permeable region 4 without endangering the capillary tube 2 itself.

In FIG. 1 the recesses 9 on the front face of the shell half 8 (and similarly those of the shell half 7) are connected by a central recess 15 which has a smaller cross-section than the recesses 9 on the front face and extends approximately across the central third of the length of the shell halves (7, 8). As can be seen from FIG. 2, the cross-sectional shapes of the central recess 15, and also the recesses 9 are matched to the cross-sectional shape of the shell halves 7 and 8, which is substantially semicircular, so that, after the shell halves 7 and 8 are placed together, there results a holding device 3 of substantially cylindrical shape with the cylindrical central recesses 15 and those 9 on the front face being of different diameter. The central recess 15 has a substantially hemispherically widened region 25 arranged approximately centrally. The passages 5 serving as measuring or observation orifices open into that region.

Spacer means 16 formed with a central bore for the capillary tube, serve to centre the capillary tube 2 with respect to the hemispherical region 25. After said spacer means 16 are pushed onto the capillary tube 2 on both sides of the light-permeable areas 4, the spacer means 16 are inserted with the capillary tube 2 into the central recess 15. The capillary tube 2 is thus fixed in the holding device 3 not only by the connector 10 but also by the spacer means 16. In particular, the spacer means 16 support the capillary tube 2 in the region of the measuring orifices and prevent deformation of the tube.

In order to be able to position the spacer means 16 quickly, accurately and regularly, the central recess 15 in the holding device 3 has an additional narrowed part opposite the recess 9 for the connector 10, with a shoulder as a stop 17 on the front face for the spacer means 16. Each shell half 7 and 8 is equipped with only one such narrowed part with a stop 17, so that the stop 17 for one spacer means is located in the shell half 7 and the one for the second spacer means 16 in the shell half 8, as shown in FIG. 1. Said arrangement of two stops 17, each of which is formed only in one shell half is sufficient to fix the annular spacer means 16 axially. The shell halves are accordingly constructed more simply, and the risk of possible deformation of the capillary tube 2 by squeezing the spacer means 16 between the stops 17 in the case of a two-sided form is avoided.

Two clamping rings 18 which fit over the outer ends of the two shell halves 7 and 8 serve to attach the two shell halves to each other. The clamping rings may be placed on the outside in the region of the connectors 10, as is shown in FIG. 1. Said clamping rings 18 in the assembled position are seated tightly on correspondingly designed cylindrical shoulders 18a of the holding device 3.

The two shell halves 7 and 8 are equipped with means for the mutually connecting them together with an accurate fit. In FIG. 2 it can be seen that the means for the accurately fitting connection of the two shell halves 7 and 8 of the holding device 3 are formed as a locating pin 19 projecting on the contact surface of one shell half and a locating opening 20 recessed at the corresponding point in the contact surface of the other shell half. In the embodiment shown, each shell half 7 and 8 has a locating pin 19 and a locating opening 20. In exactly the same way it would, however, also be possible for one shell half to have two locating pins 19 and the other shell half two locating openings 20.

It can also be seen in FIGS. 1 and 2 that sealing strips 21 are arranged along the longitudinal edges of the shell half 8 on both sides of the hemispherical area 25 as protection against unwanted light and as light seals, which can be partly sunk into grooves 22 in the contact surface of the other shell half 7. As well as protecting against unwanted light, the sealing strips 21, which are preferably elastic, also increase the total elasticity of the holding device 3 when the two shell halves 7 and 8 are placed together, which likewise serves to avoid or compensate for stress.

As is indicated in FIGS. 3 and 4, the passages 5 are preferably arranged symmetrically, in particular at right angles to each other, in each shell half 7 or 8. In principle, however, other arrangements of the passages 5 are also possible, particularly when more or less than four such passages 5 are provided.

Finally, it should be mentioned that the passages 5 continue in bushings 23 which protrude radially outwards, which bushings are preferably provided with threads, particularly external threads, to attach the photoconductor connector or light wave guide 14. This simplifies their assembly and hence the operation of the entire micro-flow cell 1 even further.

The construction of the micro-flow cell according to the invention permits stress-free assembly of the measuring capillary tube without disruptive external holding forces. The capillary tube is fixed in the holding device so that the inflow and outflow outlets are not displaced with respect to each other. The light-permeable areas of the capillary tube are simple to adjust with respect to light sources and detectors.

Measuring and connecting capillary tubes of different cross-sections can easily be combined together. Furthermore, the micro-flow cell according to the invention is so designed that fibre-optic transmission means may be used for the measuring light and the detector.

The use of fibre-optic transmission means for supplying and collecting the measuring light permits an embodiment of separate importance which is worthy of protection to the effect that the cross-sections of the photoconductors or light wave guides may be of different sizes. Thus an influence may be brought to bear simply on the changes in the refractive index of the medium in the capillary tube. Thus, for instance, changes in the refractive index of the mobile phase in the capillary tube which occur during the gradient programs which are usually used in chromatography and which are troublesome in UV detection can be minimised by the fact that the entry cross-section of the outlet photoconductor or light wave guide can be selected to be greater than that of the inlet photoconductor or light wave guide. This is extremely advantageous in particular for the LC and SFC processes mentioned at the beginning.

On the other hand, converse cross-section ratios of the optical fibers or guides may also be selected so that the micro-flow cell becomes sensitive to changes in the refractive index of the medium The cell may then be used as a refractive index detector A completely new type of field of application for the micro-flow cell according to the invention is scintillation measurement with scintillators. For this purpose glass scintillators or scintillation fibers may be used. In this, one or more scintillation fibers are fixed inside the holding device 3 in the manner described above with reference to the drawings. For instance, plastics fibers (type NE 102A) or glass fibers (type NE 901), made by Nuclear Enterprises Ltd., U.K., are used as scintillation fibers. Such micro-flow cells are used to detect traces of radioactive elements. The liquid sample flows through the micro-flow cell, the radionuclides in the liquid exciting the scintillation fibers to emit light, which is removed by one or more passages 5 and preferably passed to a photo-multiplier.

By using fibre-optic transmission elements, photoconductors, light wave guides or scintillation fibers it is possible advantageously to produce a spatial separation of the light source from the microflow cell and hence temperature regulation of the cell, which permits, for instance, detection in a supercritical medium. Equally, the flow cell may thereby be used in explosion-proof spaces.

The micro-flow cell according to the invention is designed for direct insertion into commercially available apparatus. For the reasons mentioned above it is also advantageous in such a case if photoconductors or light wave guides or optical or scintillation fibers can be used for supplying and collecting the measuring light.

We claim:

1. A micro-flow cell for chromatographic, spectrometric or scintillation measurements, comprising
    a capillary tube with an inlet and outlet and defining a flow path between said inlet and outlet for a medium to be examined,
    a holding device for said capillary tube comprising a first holding part and a second holding part, the two holding parts being designed as two substantially equal shell halves, each having a front face and a substantially semi-circular cross-section, being adapted to be secured about the length of the capillary tube to hold the latter, and being separable in their longitudinal direction along contact planes which run parallel to each other,
    at least one window for the transmission of measuring light to said tube formed in at least one of said holding parts,
    means for connecting each end of the capillary tube in a flow path for said medium, and
    means for locking said holding parts together about said capillary tube.

2. The micro-flow cell of claim 1, wherein the shell halves each have on both front faces recesses which are open at the front face and which continue into the shell halves to receive said connecting means for the capillary tube.

3. The micro-flow cell of claim 2, wherein each connecting means includes an outside elastic sleeve, which can be gripped in the recesses in the shell halves upon placing them together so that the connecting means are fixed axially and are slightly elastically displaceable radially and/or axially.

4. The micro-flow cell of claim 2, wherein the recesses on the front face of the shell halves are connected by a central recess which has a smaller cross-section than the recesses on the front face and which extends approximately across the central third of the length of the shell halves.

5. The micro-flow cell of claim 4, wherein the central recess has a substantially hemispherically widened region arranged approximately centrally.

6. The micro-flow cell of claims 5, wherein the passages open into the hemispherical region of each shell half.

7. The micro-flow cell of claim 6, wherein the cross-section of the central recess of each shell half is matched to the cross-sectional shape of the recesses on the front face and at least one spacer provided with a central bore is received in the central recess in order to centre the capillary tube with respect to the hemispherical region.

8. The micro-flow cell of claim 7, wherein a spacer is inserted on each side of the hemispherical region.

9. The micro-flow cell of claim 7, wherein the central recess of each shell half has a narrowed part with a shoulder serving as a stop for a spacer means arranged between the hemispherical region and the recess on the front face, the stops being so located that, when the holding parts are locked about the capillary tube, a spacer is arranged on each side of the hemispherical region.

10. The micro-flow cell of claims 9, wherein one of the two shell halves has sealing strips arranged along its longitudinal edges on both sides of the hemispherical region as protection against unwanted light.

11. The micro-flow cell of claim 1, wherein one holding part has two approximately radial passages arranged at an angle to each other and constituting said windows.

12. The micro-flow cell of claim 1, wherein the holding device has at least three passages the axes of which lie in a plane to which the capillary tube is normal and radially of said tube, the passages extending as far as the capillary tube and wherein at least two passages lie opposite one another and serve as measuring orifices, while the remaining passage(s) is designed for additional measurements and/or for observing the capillary tube.

13. The micro-flow cell of claim 12, wherein the holding device has four of said passages.

14. The micro-flow cell of claim 1, wherein said locking means comprises at least one clamping ring.

15. The micro-flow cell of claim 1, wherein each holding part has means for mutually connecting the two parts together with an accurate fit, such means comprising at least one locating pin projecting from the contact surface of one holding part and a locating opening recessed at the corresponding point in the contact surface of the other holding part.

16. The micro-flow cell of claim 1, wherein the capillary tube is made of glass or silica glass.

17. A micro-flow cell for chromatographic, spectrometric or scintillation measurements, comprising
    a capillary tube with an inlet and outlet and defining a flow path between said inlet and outlet for a medium to be examined,
    first and second shell halves adapted to be fitted together about the capillary tube and separable along a plane containing the axis of said tube, each shell half being formed at each end with a recess, the recesses being joined by a narrow recess formed with a hemispherical central region,
    means for connecting each end of the capillary tube in a flow path for said medium, said connecting means being located in said end recesses and including resilient means for gripping the ends of the capillary tube,
    at least one bushing on at least one of said shell halves and circumscribing a passage leading into said hemispherical central region, said passage constituting a window for the transmission of measuring light to said tube, and
    means for locking said shell halves together about said capillary tube.

18. The micro-flow cell of claim 17, and wherein there are two of said bushings and passages in one shell half and at least one of said bushing and passage in the other, the axes of said passages lying in a plane normal to the capillary tube and extending radially thereof, two of said passages lie opposite one another and serving as measuring orifices, the remaining passage(s) serving for additional measurements and/or for observing the capillary tube.

19. The micro-flow cell of claim 18, wherein said bushings which protrude approximately radially outward from the shell halves have threads to attach photoconductor connectors or light wave guides.

20. The micro-flow cell of claim 19, wherein at least one bushing is a light inlet and at least one bushing is a light outlet and wherein the crossections of the photoconductors or light wave guides at the light inlet, and the light outlet are of different sizes.

21. The micro-flow cell of claim 20, wherein the entry cross-section of the outlet photoconductor or light wave guide is greater than that of the inlet photoconductor or light wave guide.

22. The micro-flow cell of claim 20, wherein, in order to be able to use the micro-flow cell as a refractive index detector, the entry cross-section of the inlet photoconductor or light wave guide is greater than that of the outlet photoconductor or light wave guide.

23. The micro-flow cell of claim 17, wherein the capillary tube is made of glass or silica glass.

24. The micro-flow cell of claim 17, wherein one shell half has at least one locating pin and the other has at least one opening to receive said pin(s), the pin(s) and opening(s) serving to permit the two shell halves to be accurately fitted together.

25. The micro-flow cell of claim 17, wherein each shell half is formed with a longitudinal groove on each side of the narrow recess, and wherein sealing strips are arranged in the grooves as protection against unwanted light.

* * * * *